United States Patent [19]

Afflerbaugh et al.

[11] 4,202,764
[45] May 13, 1980

[54] ULTRAFILTRATION CONTROL SYSTEM

[75] Inventors: Richard L. Afflerbaugh; Wendell V. Ebling, both of Libertyville, Ill.

[73] Assignee: Baxter Travenol Laboratories, Inc., Deerfield, Ill.

[21] Appl. No.: 947,993

[22] Filed: Oct. 2, 1978

[51] Int. Cl.$^2$ .............................................. B01D 13/00
[52] U.S. Cl. .................... 210/22 D; 210/97; 210/321 B
[58] Field of Search ............... 210/22, 23, 87, 90, 210/97, 100, 103, 130, 137, 321 B, 98 M, 416 M

[56] References Cited

U.S. PATENT DOCUMENTS

| | | | |
|---|---|---|---|
| 3,441,136 | 4/1969 | Serfass et al. | 210/137 |
| 3,474,907 | 10/1969 | Cary et al. | 210/103 |
| 3,669,880 | 6/1972 | Marantz et al. | 210/23 F |
| 3,844,940 | 10/1974 | Kopf et al. | 210/96 M |
| 3,878,095 | 4/1975 | Frasier et al. | 210/87 |
| 3,976,574 | 8/1976 | White | 210/321 A |
| 3,979,284 | 9/1976 | Granger et al. | 210/22 |
| 3,990,973 | 11/1976 | Boag et al. | 210/87 |
| 4,021,341 | 5/1977 | Cosentino | 210/103 |
| 4,113,614 | 9/1978 | Rollo et al. | 210/90 |

FOREIGN PATENT DOCUMENTS 2745348   4/1978   Fed. Rep. of Germany ........... 210/137

*Primary Examiner*—Charles N. Hart
*Assistant Examiner*—E. Rollins Cross
*Attorney, Agent, or Firm*—Paul C. Flattery; Gerald S. Geren

[57] ABSTRACT

There is disclosed herein a dialysis machine for use with a negative-pressure-type dialyzer. The machine includes a flow system for drawing fresh dialysis solution, under a negative pressure, through the dialyzer and a system for determining, setting and controlling ultrafiltration rates in the dialyzer. The ultrafiltration system includes a branch for communication with the dialyzer when flow to and from the dialyzer is terminated. In the branch there is provided a pump for applying negative pressure to the dialyzer and drawing liquid therethrough, and a meter for measuring the flow rates. Means are also provided for measuring negative pressure and transmembrane pressure during operation of the ultrafiltration branch. Pressure controls are also provided so as to assure maintenance of the ultrafiltration rates.

There is also disclosed herein a method for determining, setting and controlling the ultrafiltration rate. The method includes terminating flow of dialysis solution to and from the dialyzer, drawing liquid from the dialyzer in order to establish a desired ultrafiltration rate and maintenance of that ultrafiltration rate during actual dialysis by appropriate pressure controls and adjustment of negative pressure and transmembrane pressure.

14 Claims, 1 Drawing Figure

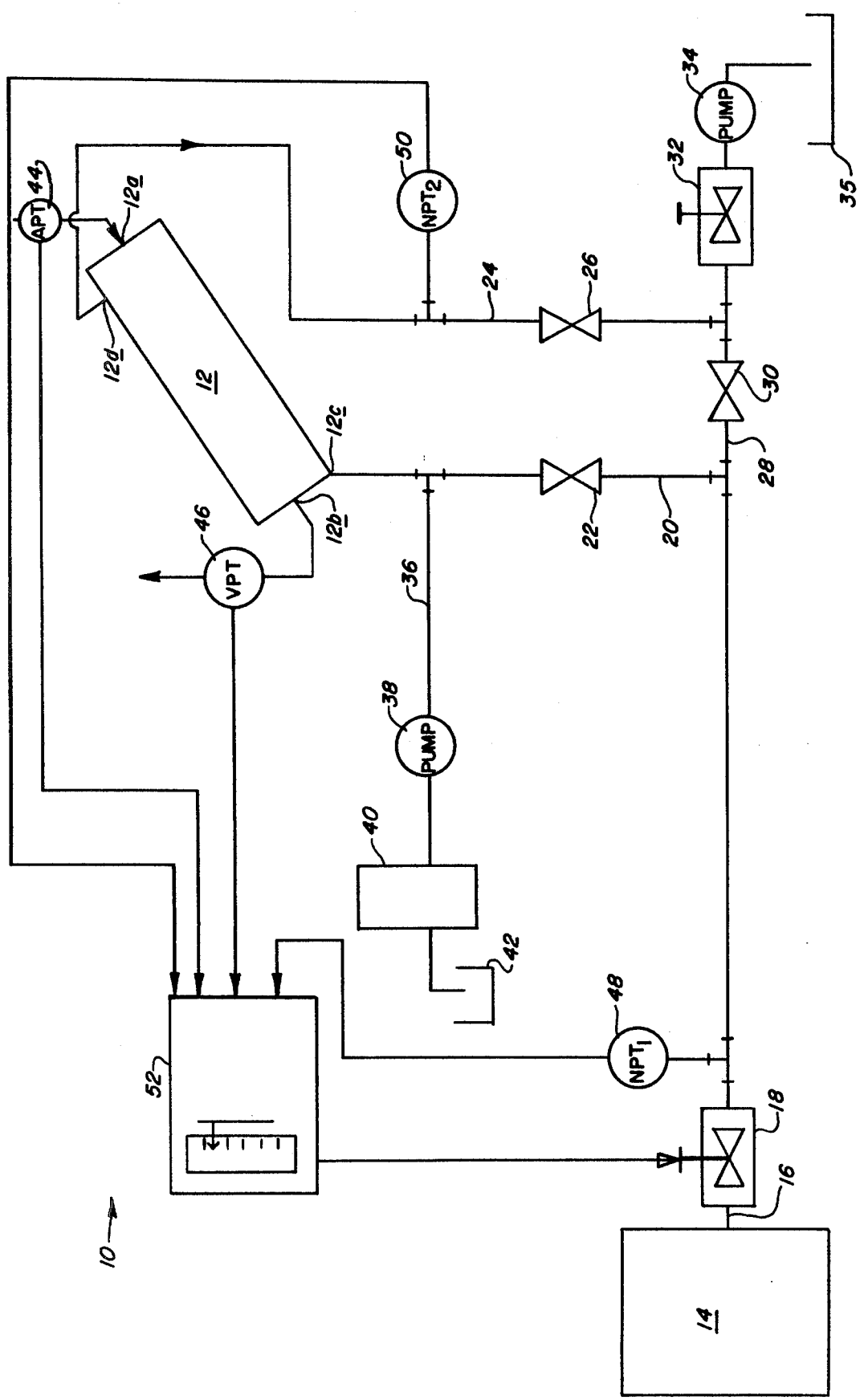

ULTRAFILTRATION CONTROL SYSTEM

FIELD OF THE INVENTION

This invention relates to artificial kidney systems, and more particularly, to a method and apparatus for controlling the ultrafiltration rate in a single-pass or flow-through negative-pressure type dialysis system.

BACKGROUND OF THE INVENTION

Artificial kidney systems include a dialyzer and a dialysis machine which controls the operation of the dialyzer. The dialyzer is used to treat a patient's blood so as to remove water and waste products therefrom. The dialyzer includes a semipermeable membrane which separates blood and dialysis solution flowing through the dialyzer. Waste product removal occurs by mass transfer through the membrane and water removal occurs by ultrafiltration through the membrane.

In some dialysis machines the dialysis solution is drawn through the dialyzer under a negative pressure (i.e., below atmospheric pressure). Such machines normally include a negative pressure pump positioned downstream of the dialyzer for drawing the dialysis solution through the dialyzer and an adjustable negative pressure valve positioned upstream of the dialyzer for controlling the negative pressure in the dialyzer. One such machine is disclosed in U.S. Pat. No. 3,878,095 Frasier et al. A commercial machine embodying such a system is manufactured and sold by Baxter Travenol Laboratories and is identified as Proportioning Dialyzing Fluid Delivery System (5M 1352-5M 1355).

In the single-pass or flow-through machines, dialysis solution is either continuously prepared or is prepared in batches. The fresh dialysis solution is drawn through the dialyzer, through the machine and is discharged to a drain. There is also a second type of negative pressure system, known as the closed-loop system, in which a fixed volume of dialysis solution continuously recirculates through the dialyzer, and thus it is necessary to remove waste products from the solution by appropriate cleansing or regenerating apparatus.

The removal of water from the blood by the process of ultrafiltration relies on the pressure differential across the semipermeable membrane (i.e., the difference in pressure of the blood flowing under positive pressure through the dialyzer and the dialysis solution flowing under a negative pressure through the dialyzer). This pressure differential is commonly known as the transmembrane pressure and the amount of water removed from the blood is directly related thereto.

It is known to be desirable to control the amount of and the rate at which water is removed from the patient, since the removal of too much water at too fast a rate can result in one type of a side effect and water removal at too slow a rate can result in a different type of a side effect. In some existing systems, the ultrafiltration rate is related only to negative pressure. This relation is less accurate than relating the ultrafiltration to transmembrane pressure, since no provision is made for changes in blood pressure which affect the transmembrane pressure and thus the ultrafiltration rate.

U.S. Pat. Nos. 3,844,940; 3,979,284; and 3,990,973 appear to be representative of existing ultrafiltration systems. These patents disclose, for example: closed-circuit systems which require regeneration; systems relating ultrafiltration only to negative pressure; and an electrical measuring system having related transmembrane pressure controls.

However, the existing systems have not provided a desirable structure for use in a flow-through type machine as described above for determining, setting and controlling the rate of ultrafiltration.

It is therefore an object of this invention to provide an ultrafiltration system which permits accurate and controllable determination and setting of the ultrafiltration rate.

It is another object of this invention to also provide a system for controlling and relating ultrafiltration to transmembrane pressure.

These and other objects and advantages of this invention will become apparent from the following description and appended claims.

SUMMARY OF THE INVENTION

There is disclosed herein a method and apparatus for determining and controlling the rate of ultrafiltration in a flow-through dialysis system and for relating the ultrafiltration rate to transmembrane pressure. The apparatus includes an ultrafiltration monitoring line or branch having a variable speed pump, a flow meter and a discharge to drain. A pressure transducer is also provided for cooperation with the branch to determine negative pressure in the branch during the ultrafiltration set-up mode.

In normal operation, the dialyzer is positioned at an angle to the horizontal with the dialysis solution inlet being lower than the outlet so as to assure that gas bubbles, if any, migrate to the outlet for removal. It has been found that connection of the ultrafiltration branch to the inlet side is very desirable, since such connection minimizes the possibility of drawing gas bubbles through the ultrafiltration branch. It is undesirable to draw the bubbles through the branch since they may cause a false reading by inflating the value of the quantity of liquid flowing through the branch.

The method includes the steps of terminating dialysis solution flow to and from the dialyzer, operating the variable speed pump to obtain an ultrafiltration rate as shown by the flow meter, detecting the negative pressure in the ultrafiltration line during the measurement and determining the transmembrane pressure for the desired ultrafiltration rate. Thereafter, dialysis solution flow to and from the dialyzer is re-established, operation of the ultrafiltration monitoring line is stopped, and the actual transmembrane pressure is controlled to the previously determined value.

BRIEF DESCRIPTION OF THE DRAWING

The drawing is a diagrammatic representation of a dialysis system which includes an ultrafiltration monitoring line or branch and appropriate transmembrane pressure controls.

DESCRIPTION OF THE PREFERRED EMBODIMENT

Referring now to the drawing, there is shown a dialysis system 10 generally. The system can be viewed as including three different sections. Those sections are: the standard flow system; the ultrafiltration branch; and the transmembrane control system.

The Flow System

The flow system includes a dialyzer 12 that has a semipermeable membrane which separates blood flowing through the dialyzer from dialysis solution. Such dialyzers may be of either the parallel-plate-type or the hollow-fiber type. Blood enters the dialyzer via inlet 12a and exits via outlet 12b, and dialysis solution enters via inlet 12c and exits via outlet 12d. In normal operation, the dialyzer is tipped so that the outlet 12d is above the inlet 12c so as to aid in removal of any gas bubbles formed in the dialyzer during dialysis.

Upstream of the dialyzer there is provided a supply 14 for dialysis solution. The supply can either be a reservoir for previously prepared batches of solution or, in the alternative, can be freshly mixed by the known proportioning-type devices. Fresh dialysis solution flows from the supply 14 along a main flow conduit 16 through an adjustable negative pressure valve 18 to an inlet line 20 that leads to the dialyzer 12. An inlet valve 22 is positioned in the inlet line upstream of the dialyzer for permitting or terminating flow to the dialyzer. Spent dialysis solution exits the dialyzer via outlet line 24 and an outlet valve 26 is provided for permitting or terminating flow of dialysis solution from the dialyzer. A bypass line 28 is provided which also includes a bypass valve 30 that permits flow to bypass the dialyzer. The bypass line 28 bridges or is connected across the inlet line 20 and outlet line 24.

An adjustable flow control valve 32 is positioned downstream of the valves 26 and 30 for receiving and controlling flow. A constant-speed negative-pressure pump 34 is positioned downstream of the control valve 32 for drawing dialysis solution from the supply through the dialyzer. Alternatively, a variable-speed pump can be substituted for the control valve 32 and the constant-speed pump 34 to control liquid flow. The spent or used dialysis solution is discharged from the dialysis system to the drain 35.

The Ultrafiltration Branch

The ultrafiltration branch is a flow-through system and includes a flow line 36 which is connected to the dialysis solution inlet line 20 between the inlet valve 22 and the dialyzer 12. A variable-speed ultrafiltration pump 38 is provided for drawing dialysis solution through the line 36 and adjusting the negative pressure in the system. A flow meter 40 is provided downstream of the pump 38 for displaying the rate of liquid flow through the ultrafiltration branch. The meter 40 may be positioned upstream of the pump 38, and in that position, any possible effect of outgassing is minimized. The rate of liquid flow through the pump 38 and meter 40 during operation in the ultrafiltration mode corresponds to the ultrafiltration rate. Liquid drawn through the ultrafiltration line is discharged from the ultrafiltration line to a drain 42.

Pressure Detectors

Pressure conditions within the dialyzer on both the blood and the dialysis solution side are continuously monitored. An arterial pressure transducer (APT) 44 monitors the incoming blood pressure and the venous pressure transducer (VPT) 46 monitors returning blood flow. There are also provided two negative pressure transducers which bracket the dialyzer and measure negative pressure. The upstream negative pressure transducer ($NPT_1$) 48 measures pressure between the valve 18 and the inlet valve 22, while the downstream negative pressure transducer ($NPT_2$) 50 measures the pressure between the dialyzer and the outlet valve 26.

The Transmembrane Pressure Control

The transmembrane pressure control system includes a transmembrane pressure controller 52 which receives the output signal from each of the pressure transducers 44, 46, 48 and 50. A desired transmembrane pressure can be entered into the controller and the controller can adjust the actual transmembrane pressure to the desired pressure.

The mean blood pressure within the dialyzer is determined by averaging the outputs of the arterial pressure transducer 44 and venous pressure transducer 46. The mean negative pressure in the dialyzer is determined by averaging the outputs of the upstream negative pressure transducer 48 and the downstream negative pressure transducer. These mean pressures are added algebraically so as to determine the transmembrane pressure control.

In the ultrafiltration mode, the transmembrane pressure is determined by averaging the output of the arterial and venous pressure transducers and adding that algebraically to the output of the downstream negative pressure transducer.

The negative pressure control valve 18 is also connected to the transmembrane pressure controller 52. Control of the actual transmembrane pressure is made by adjusting the valve 18 so as to maintain a predetermined transmembrane pressure. The adjustment is made by the controller comparing (1) the actual transmembrane pressure as approximated by the mean blood pressure and mean negative pressure with (2) the predetermined transmembrane pressure value which is determined during ultrafiltration measurement and entered into the controller and (3) then opening or closing the negative pressure valve 18 to minimize any differences between the actual and predetermined pressures. The specific construction for such controls is known and can be either manual or automatic.

Operation

In normal operation, sometimes referred to as the dialyze mode, blood flows through the dialyzer and the negative pressure pump 34 draws dialysis solution from the supply 14, through the adjustable valve 18, through the inlet line 20 and through the dialyzer 12. From the dialyzer the spent dialysis solution flows via line 24, through valve 32, pump 34, and to the drain. Negative pressure within the dialyzer is controlled by adjusting the adjustable negative pressure valve 18 to obtain the desired negative pressure. During normal operation, the valves 22 and 26 are open so as to permit flow to and from the dialyzer. However, under certain predetermined conditions, the valves 22 and 26 are closed so as to terminate flow to and from the dialyzer, thereby isolating the dialyzer from the flow system and the bypass valve 30 is simultaneously opened so as to permit flow directly from the supply 14 to the pump 34.

When it is desired to determine or set the ultrafiltration rate, the machine is removed from the dialyze mode and is operated in the ultrafiltration set-up mode. In the set-up mode, valves 22 and 26 are closed so as to isolate the dialyzer and bypass valve 30 is opened. Blood still continues to flow through the blood side of the dialyzer. The ultrafiltration pump 38 is activated and adjusted until a desired or predetermined ultrafiltration rate is achieved. That rate is displayed on the meter 40. In such operation the only liquid flowing through the branch is water flowing across the membrane from the blood into the dialysis solution. Thus that flow rate is the ultrafiltration rate. When the desired ultrafiltration rate is obtained, the negative pressure indicated by the downstream negative pressure transducer 50 is noted and added algebraically to the mean blood pressure as determined from the signals from the transducers 44 and 46. This value is automatically determined and entered in the controller 52 and represents the transmembrane pressure which will provide the desired ultrafiltration rate.

The machine is then returned to the dialyze mode, thereby inactivating the ultrafiltration branch, opening the valves 22 and 26, closing the bypass valve 30, and allowing the pump 34 to draw dialysis solution through the system.

In the dialyze mode the transmembrane pressure control system compares the entered transmembrane pressure value and actual pressure conditions as noted by the pressure transducers 44, 46, 48 and 50, and then operates the valve 18 to control the valve 18 and the negative pressure, in such a manner as to maintain the actual transmembrane pressure at a value approximating the entered transmembrane pressure.

The operator of the dialysis machine may decide at various times during the dialysis treatment that, because of changing conditions in the dialyzer, the patient's condition, etc., that it is necessary to re-measure the ultrafiltration rate and/or reset the ultrafiltration rate. In order to reset the ultrafiltration rate, the system is returned to the ultrafiltration set-up mode in which flow to the dialyzer is prevented by closing valves 22 and 26 and the ultrafiltration branch and pump 38 are then activated. The previously described procedure is then followed to establish an ultrafiltration rate and determine a desired transmembrane pressure. Automatic operation is anticipated to achieve some functions which the operator may perform manually.

It will be appreciated that numerous changes and modifications may be made to the embodiment disclosed herein without departing from the spirit and scope of this invention.

What is claimed is:

1. A dialysis machine that is adapted for operation with a negative pressure-type dialyzer which has a semipermeable membrane that separates dialysis solution and blood flowing through said dialyzer, said machine including:
   (a) a flow system which includes negative pressure pump means for drawing fresh dialysis solution under a negative pressure from a source through said dialyzer and for discharging the spent dialysis solution to a drain;
   wherein the improvement comprises, in combination:
   (b) valve means positioned in said flow system for isolating said dialyzer from said negative pressure pump means, and for terminating flow of dialysis solution to and from said dialyzer;
   (c) means defining an ultrafiltration branch connected to the flow system between the dialyzer and the valve means for communication with said dialyzer when said dialyzer is isolated and flow is terminated and for drawing liquid from said dialyzer, said ultrafiltration branch including:
      (i) ultrafiltration pump means for drawing and controlling the flow of liquid from the dialyzer so as to adjustably establish an ultrafiltration rate;
      (ii) means for measuring the liquid flow rates in said branch; and
   (d) means associated with said branch and said dialyzer for measuring the pressure on the blood and dialysis solution sides of the dialyzer at the time the desired ultrafiltration rate is established and for determining a transmembrane pressure.

2. A system as in claim 1, wherein said ultrafiltration branch is connected to the flow system between the dialyzer and the valve means controlling flow to the dialyzer.

3. A system as in claim 2, wherein said ultrafiltration branch further includes drain means for discharging liquid flowing into said branch from a dialyzer.

4. A dialysis machine as in claim 1, wherein said ultrafiltration pump means controls the flow of liquid by adjustably applying negative pressure to said dialyzer.

5. A dialysis machine as in claim 1, wherein said means for measuring flow rates comprises a flow meter positioned in said branch downstream of said ultrafiltration pump means.

6. A dialysis machine as in claim 1, wherein said means for measuring dialysis solution pressure includes a downstream negative pressure transducer positioned in said flow system between said dialyzer and said valve for terminating flow from said dialyzer.

7. A dialysis machine as in claim 1, further including means for controllably adjusting the actual transmembrane pressure to the determined pressure so as to maintain the desired ultrafiltration rate.

8. A system as in claim 7, wherein there is further provided a negative pressure control valve in said flow system operatively associated with said transmembrane pressure control means and constructed for adjustment in response to changes in the transmembrane pressure.

9. A method for determining, setting and controlling the ultrafiltration rate in a negative pressure-type dialyzer which has a semipermeable membrane with dialysis solution flowing through said dialyzer on one side of the membrane under a negative pressure and blood flowing on the other side of said membrane and inlet and outlet lines for carrying blood and dialysis solution to and from said dialyzer, said method comprising the steps of:
   flowing blood and dialysis solution through said dialyzer;
   terminating flow of dialysis solution to and from said dialyzer so as to isolate said dialyzer;
   thereafter drawing liquid from said dialyzer;
   determining the flow rate of liquid drawn from said dialyzer;
   adjusting the liquid flow rate to obtain a desired ultrafiltration flow rate;
   determining a transmembrane pressure related to the desired ultrafiltration rate;
   re-establishing dialysis solution flow through said dialyzer; and
   thereafter controlling the actual transmembrane pressure during normal operation so as to approximate the predetermined transmembrane pressure.

10. A method as in claim 9, wherein said transmembrane pressure is determined by measuring the pressures on the blood side and on the dialysis solution side of the dialyzer membrane and determining the difference in pressures which is equivalent to the transmembrane pressure.

11. A method as in claim 9, wherein the liquid is drawn from the dialyzer under a negative pressure and the flow rate from the dialyzer is adjusted by adjusting the negative pressure.

12. A method as in claim 11, wherein the transmembrane pressure is determined by measuring the negative pressure at which the desired flow rate is obtained and the blood pressure and determining the difference therebetween.

13. A method as in claim 12, wherein the actual transmembrane pressure during normal operation is controlled by adjusting the negative pressure drawing dialysis solution through the dialyzer.

14. A method as in claim 9, wherein said liquid is drawn from the dialyzer on the side through which dialysis solution enters the dialyzer.

* * * * *